(12) United States Patent
Hussain

(10) Patent No.: US 6,732,456 B2
(45) Date of Patent: May 11, 2004

(54) SHOE INSERTS WITH BUILT-IN STEP INDICATING DEVICE

(76) Inventor: Shakil Hussain, 3926, 205th Pl. SW., Lynnwood, WA (US) 98036

( * ) Notice: Subject to any disclaimer, the term of this patent is extended or adjusted under 35 U.S.C. 154(b) by 0 days.

(21) Appl. No.: 10/102,260

(22) Filed: Mar. 20, 2002

(65) Prior Publication Data

US 2003/0177667 A1 Sep. 25, 2003

(51) Int. Cl.[7] .................................................. A61F 5/14
(52) U.S. Cl. ............................. 36/144; 36/140; 36/173
(58) Field of Search ........................... 36/140, 143, 144, 36/172, 173, 174, 175, 176, 178

(56) References Cited

U.S. PATENT DOCUMENTS

| | | |
|---|---|---|
| 2,255,100 A | 9/1941 | Brady |
| 3,861,398 A | 1/1975 | Leydecker |
| 4,232,457 A | 11/1980 | Mosher |
| 4,360,027 A | 11/1982 | Friedlander et al. |
| 4,446,633 A | 5/1984 | Scheinhaus et al. |
| 4,510,700 A | 4/1985 | Brown |
| 4,597,196 A | 7/1986 | Brown |
| 4,702,255 A * | 10/1987 | Schenkl ........................ 36/145 |
| 4,718,179 A * | 1/1988 | Brown .......................... 36/44 |
| 4,747,410 A | 5/1988 | Cohen |
| 4,759,357 A | 7/1988 | Allart et al. |
| 4,869,001 A * | 9/1989 | Brown ......................... 36/115 |
| 4,972,611 A * | 11/1990 | Swartz et al. .................. 36/28 |
| 4,979,318 A | 12/1990 | Cohen |
| 5,174,052 A | 12/1992 | Schoenhaus et al. |
| 5,220,737 A | 6/1993 | Edington |
| 5,247,742 A | 9/1993 | Kilgore et al. |
| 5,544,432 A | 8/1996 | Kita |
| 5,564,989 A * | 10/1996 | Larsen ......................... 36/127 |
| D383,894 S * | 9/1997 | Snyder et al. ............... D2/961 |
| 5,778,560 A | 7/1998 | Danieli |
| 6,038,793 A | 3/2000 | Kendall |
| 6,226,901 B1 | 5/2001 | Rosen |
| 6,269,554 B1 | 8/2001 | Silvestrini et al. |
| 6,314,662 B1 | 11/2001 | Ellis, III |
| 6,360,597 B1 | 3/2002 | Hubbard, Jr. |

* cited by examiner

*Primary Examiner*—Ted Kavanaugh

(57) ABSTRACT

A shoe insert of the orthotic type made of a flexible material to enable repeated flexing without cracking and having a built-in step indicating device made of a stiff material that indicates to the user the posture or orientation of the foot at initial heel-to-ground contact through final toe-off.

5 Claims, 5 Drawing Sheets

SHOE INSERTS WITH BUILT-IN STEP INDICATING DEVICE

BACKGROUND OF THE INVENTION

1. Field of the Invention

The present invention pertains to footwear and, more particularly, to a shoe insert that incorporates an indicator of foot posture.

2. Description of the Related Art

Excessive pronation (inward roll) and supination (outward roll) of the foot are commonly known to cause problems such as heel pain, aching legs, knee pain and back pain. This roll action or rotation of the foot is undesirable and is caused by the prolonged improper way of how a person executes each step in the process of walking, running or in any other activity. As a result, the person unknowingly loses having the correct step dynamics and the problem deteriorates over time. When the foot rolls out of alignment from its normal position, a chain of unpleasant events occur. In the case of a pronating foot, the arch is lowered or collapses, causing the plantar fascia ligament which extends from the heel bone to the base of the toes to stretch. The increased strain due to the stretching of the plantar fascia ligament may cause inflammation of the ligament with resulting small tears at the heel attachment point, causing heel pain. In both cases of excessive pronation and supination, the misaligned foot causes the leg to rotate out of alignment. The imbalance on the leg puts uneven forces on the knee joint causing knee pain. Further up the leg, the pelvis is forced out its normal alignment in order to carry and transfer the imbalanced load from the misaligned leg to the back. The misaligned pelvis causes an increase in the curvature of the backbone resulting in poor body posture and therefore back pains. A person may not be aware that his or her feet are rotated out of alignment even while standing at a stationary position.

There are many types of orthotic shoe inserts available in the market today. Some inserts attempt to correct the misalignment of the foot by merely forcing the foot back to its normal position. While other inserts simply provide better support, comfort and control over excessive pronation (inward roll) or supination (outward roll) of the feet.

U.S. Pat No. 4,510,700 to Brown (1985) and U.S. Pat. No. 5,174,052 to Schoenhaus, et al. (1992) are two examples of such orthotic shoe inserts which basically provide the feet with similar support and roll control. These shoe inserts however are only beneficial when used. In reality, the common person does not wear shoes throughout the day or the night and therefore does not wear shoe inserts throughout the day or the night.

As one who used to suffer from excessive supination of the feet, the inventor searched for a footwear product that could train a user by indicating the posture or orientation of the feet at ground contact while walking, running, standing or while doing any other activity so that the user could correct the posture of the feet by rotating them back to their normal position.

The present shoe inserts suffer from a number of disadvantage:

(a) They do not provide any form of indication to the user with regards to the posture or orientation of the foot at ground contact.

(b) They benefit the user only when used.

(c) The present shoe inserts makes the user highly dependent on them since they do not provided a permanent solution.

(d) The present shoe inserts do not remove the problem of excessive pronation and supination of the foot. They only accommodate the problem by realigning the foot or by giving it better support.

BRIEF SUMMARY OF THE INVENTION

In accordance with the present invention, an orthotic shoe insert is provided that includes a built-in-step indicating device which indicates excessive pronation and supination of the foot. In one embodiment, the indicating device is formed of at least one bead on the bottom surface of the heart.

The features and advantages of the invention includes:

(a) An orthotic shoe insert that will give an indication to the user the posture or orientation of the ground contact while walking, running, standing or while doing any other activity.

(b) A shoe insert that trains the user to self-correct any misalignment due to the rotation of the foot.

(c) An orthotic shoe insert that will enable the user, after a period of time, to be free from having to rely on shoe inserts as soon as the user is naturally able to control foot rotations.

(d) A shoe insert which aims to remove the root cause of the problem of excessive pronation and supination of the foot.

As will be readily appreciated from the foregoing, the orthotic shoe insert of the present invention will help in reducing or removing the problems caused by or related to excessive pronation or supination of the feet.

BRIEF DESCRIPTION OF THE SEVERAL VIEWS OF THE DRAWING(S)

The foregoing features and advantages of the disclosed embodiments of the invention will be more readily appreciated as the same become better understood from the accompanying drawings wherein like elements are referred to with the identified reference number but different alphabetical suffix.

DETAILED DESCRIPTION OF THE INVENTION

Figure 1:
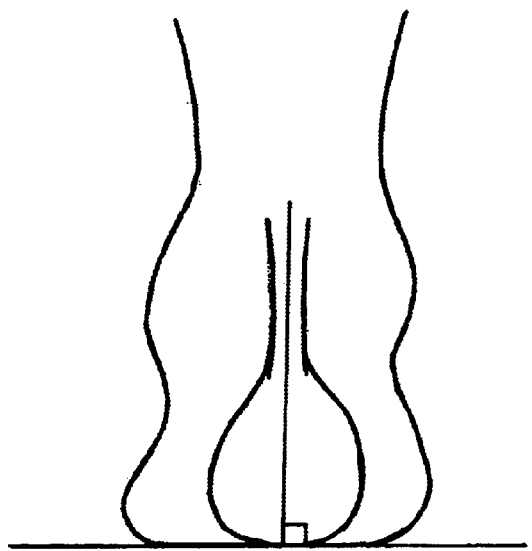
FIG. 1 shows the rear view of a normal right foot.
Figure 2:
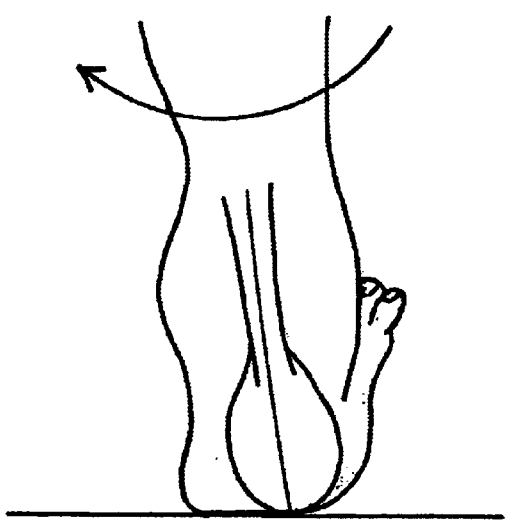
FIG. 2 shows the rear view of a pronating right foot.
Figure 3:
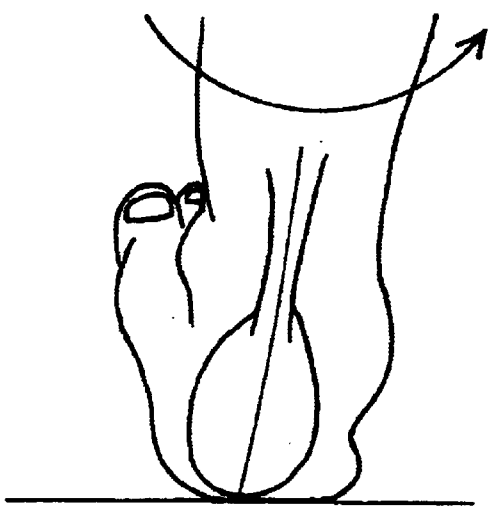
FIG. 3 shows the rear view of a supinating right foot.
Figure 4:
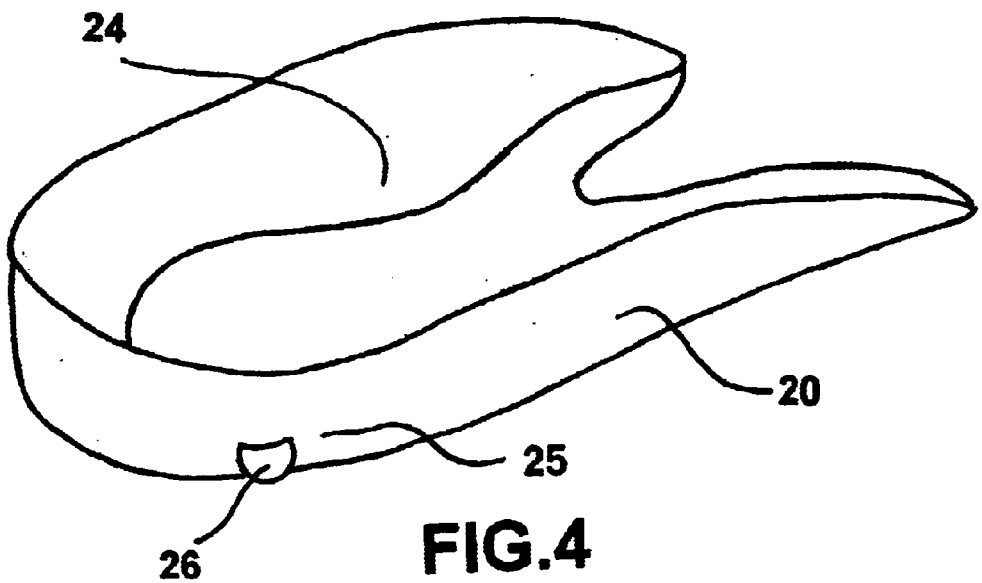
FIG. 4 shows a perspective view of a right shoe insert with the indicator device located near the outer edge.
Figure 6:
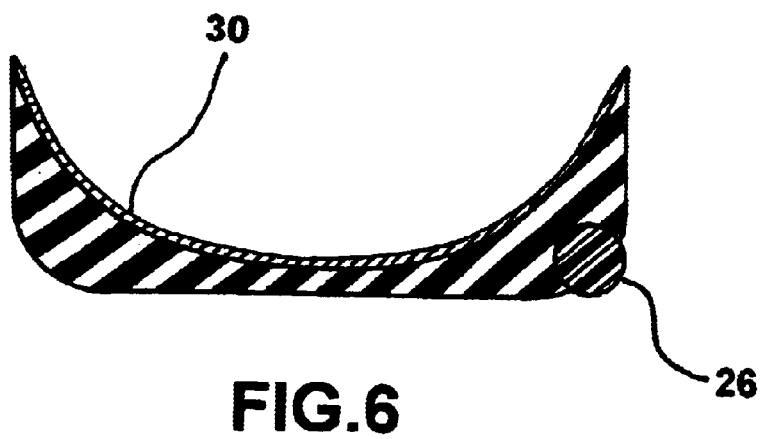
FIG. 6 shows a sectional view of the shoe insert.

A representative embodiment of a shoe insert of the present invention is illustrated in FIG. 4, which shows a right foot shoe insert 20. The same description and principles apply to the left foot shoe insert but as a mirror image of the right foot shoe insert. The indicator device 26 in FIG. 4 is located near the outer edge 25 of the shoe insert 20. The shoe insert 20 is made of a flexible material which can repeatedly flex in the process of walking or running without cracking or fracturing and continues to retain its original shape afterwards. In the preferred embodiment, the shoe insert 20 is a flexible polyurethane foam. However, the shoe insert 20 can be made of any other durable material that can withstand the relevant forces related to the human body in motion and repeatedly flex without cracking or fracturing, such as polypropylene, polyurethane foam, nylon, rubber, leather, various impregnated or laminated fibrous materials, various plasticized materials, etc. As shown in FIG. 6, the cross-section of the shoe insert 20 is basically U-shaped from the heel location and gradually flattens out towards the toe. As shown in FIG. 6, the insert has a first thickness under the heel of a user and a second substantially greater thickness along an outer perimeter edge of the insert.

In the preferred embodiment, the indicator device 26 comprises of a bead of material and is spherical in shape. It is made of solid hard plastic material. However the indicator device 26 can also be made of any other suitable material such as vinyl, nylon, rubber, plasticized material, laminated fibrous materials, etc.

An arch support 24 is built into the design of the insert 20 to provide better support and comfort. The arch support 24 together with the insert 20 can be integrally made in the process of manufacture, such as molding.

Figure 5:
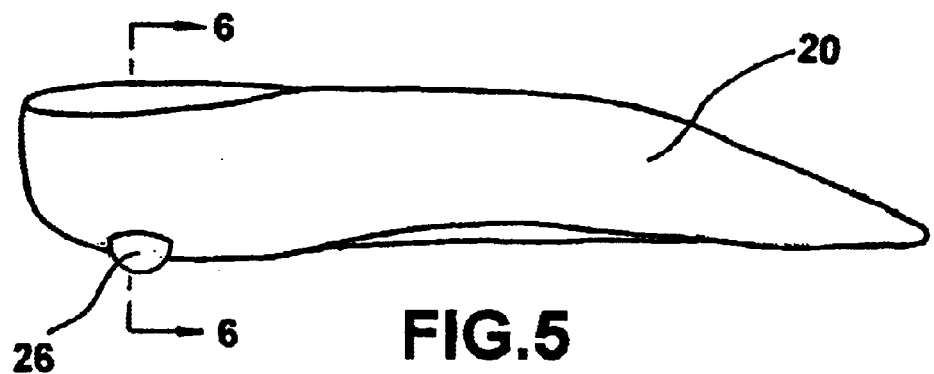
FIG. 5 shows the side view of a right shoe insert with the indicator device located near the outer edge.

The indicator device 26 can be located on various locations on the insert 20, as shown in FIGS. 4, 5 and 6. It can either be bonded to the shoe insert 20 in a separate process or it can be molded in place simultaneously in a single process during the manufacture of the inserts.

Figure 8A:
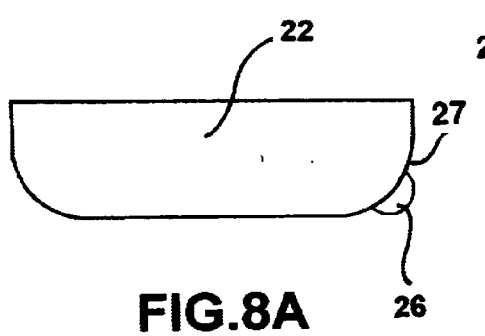
FIGS. 8A and 8B show the rear view of a pair of left and right shoe inserts with the indicator device located near the inner edges of the shoe inserts.
Figure 8B:
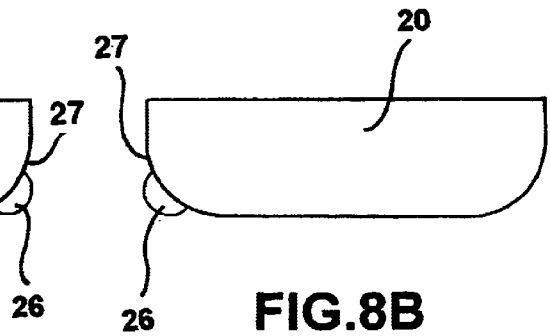
Figure 9A:
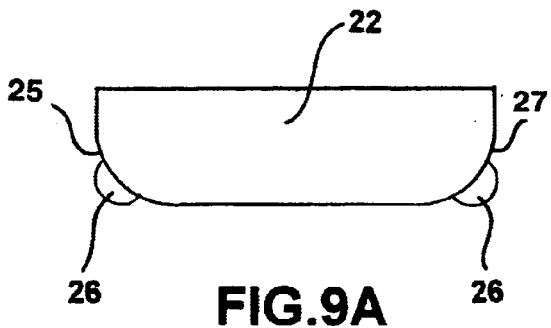
FIGS. 9A and 9B show the rear view of a pair of left and right shoe inserts with the indicator device located near both the inner and outer edges of the shoe inserts.
Figure 9B:
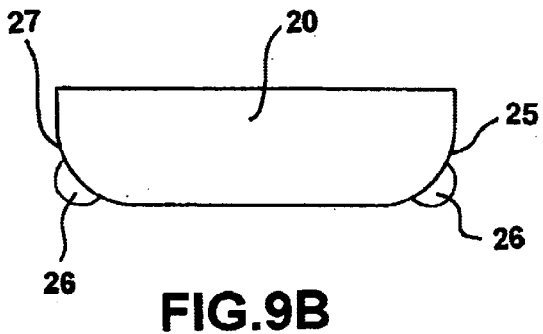

Additional embodiments are shown in FIGS. 8A and 8B where the indicator devices 26 are located near the inner edges 27 of the right shoe insert 20 and left shoe insert 22. In FIGS. 9A and 9B, the indicator devices 26 are located near both the inner edge 27 and outer edge 25 of the shoe inserts.

Figure 14:
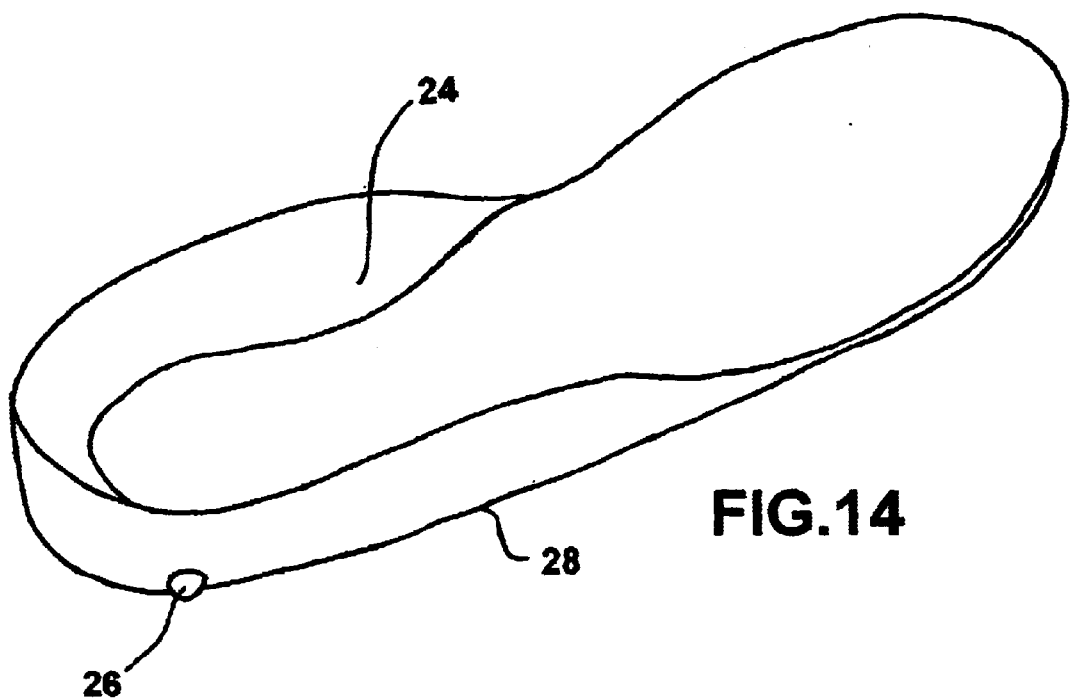
FIG. 14 shows a perspective view of a full-length version of a right shoe insert with the indicator device located near the outer edge.

An alternative embodiment is shown in FIG. 14, which is similar to FIG. 4, except that the shoe insert 28 shown is of a full-length version.

From the description above, a number of advantages of the shoe insert with built-in step indicating device become evident:

(a) The indicator device 26 is a simple single piece object which can be cheaply made from readily available materials such as plastic, vinyl, nylon, rubber, plasticized material, laminated fibrous materials, etc.

(b) The technology to manufacture these shoe inserts is readily available. Therefore no additional cost would be incurred in having to develop new equipment or machines.

Figure 15:
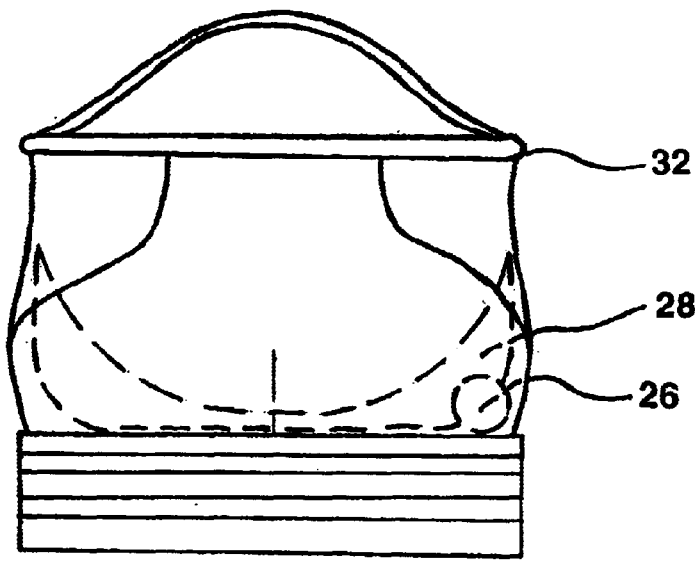
FIG. 15 shows the rear view of a shoe with the insert in position.

The manner of using these shoe inserts 20, 22 is identical to that for shoe inserts in present use. The left and right inserts 22, 20, respectively, are placed in the respective left and right shoes, which are then worn by the user. A view of the insert 28 in position in a shoe 32 is shown in FIG. 15.

Figure 7A:
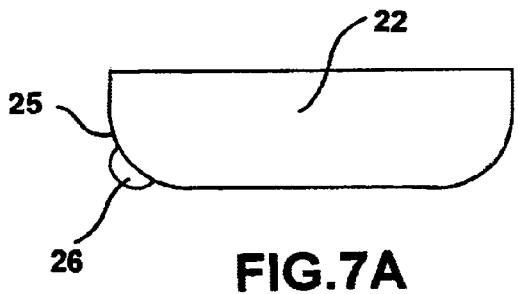
FIGS. 7A and 7B show the rear view of a pair of left and right shoe inserts with the indicator device located near the outer edges of the shoe inserts.
Figure 7B:
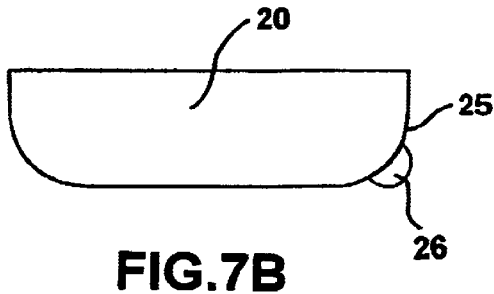
Figure 10:
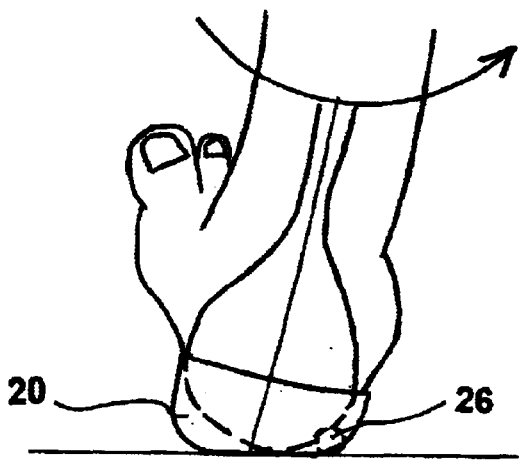
FIG. 10 shows the rear view of a right foot in an outward roll (supinated) position with the indicator device located near the outer edge of the shoe insert.
Figure 11:
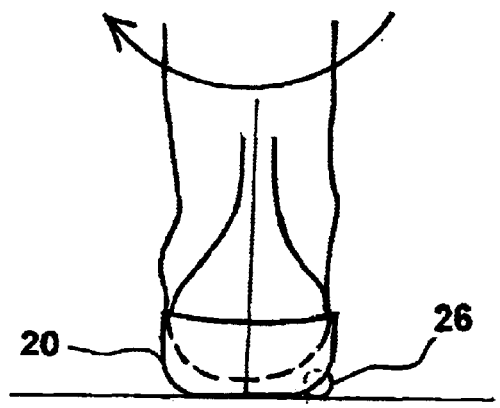
FIG. 11 shows the rear view of a right foot in a normal position with the indicator device located near the outer edge of the shoe insert.
Figure 12:
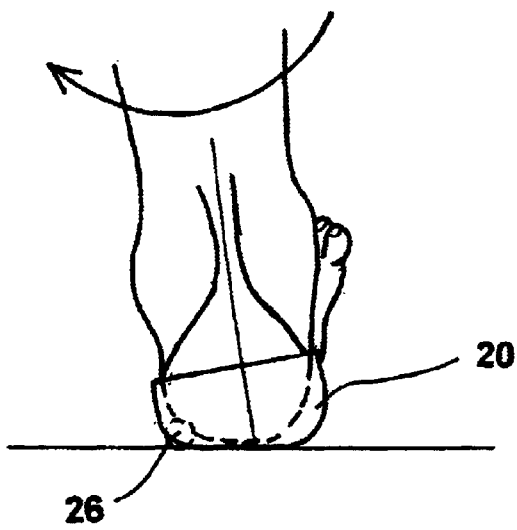
FIG. 12 shows the rear view of a right foot in an inward roll (pronated) position with the indicator device located near the inner edge of the shoe insert.
Figure 13:
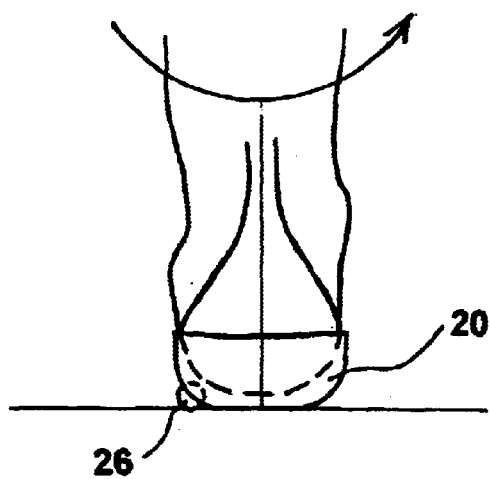
FIG. 13 shows the rear view of a right foot in a normal position with the indicator device located near the inner edge of the shoe insert.

When in indicator devices 26 are located near the outer edges of the inserts 20 and 22 as shown in FIGS. 7A and 7B, such shoe inserts are meant for those who suffer from excessive supination or outward roll of the feet. When the foot is in the outward roll position, the outer edge of the shoe comes in contact with the ground first. Since the indicator device 26 is located on the outer edge 25 of the inserts 20 and 22, the user will feel a mild "poking" sensation on the user's outer heel edge due to the pressure of the foot on the indicator device 26 at ground contact as shown in FIG. 10. This would give an indication to the user that an inward counter roll or rotation of the foot is needed in order to correct the posture of the foot sufficiently so that the "poking" sensation is no longer felt as shown in FIG. 11. The size, depth and position of the indicator device 26 can be varied to enables the user to determine the amount of counter roll or rotation required in order to bring the foot back to its normal position, depending on the severity of the problem.

Where the indicator devices 26 are located near the inner edges 27 of the inserts 20 and 22 as shown in FIGS. 8A and 8B, such shoe inserts are meant for those who suffer from excessive pronation, or inward roll of the foot. When the foot is in the inward roll position, the inner edge of the shoe comes in contact with the ground first. Since the indicator device 26 is located near the inner edge of the inserts 20 and 22, the user will feel a mild "poking" sensation on the user's inner heel edge due to the pressure of the foot on the indicator device 26 at ground contact as shown in FIG. 12. This would give an indication to the user that an outward counter roll or rotation of the foot is needed in order to correct the posture of the foot sufficiently so that the "poking" sensation is no longer felt as shown in FIG. 13.

Where the indicator devices 26 are located near both the inner edge 27 and outer edge 25 of the inserts 20 and 22 as shown in FIGS. 9A and 9B, such shoe inserts are designed to address the case where the user needs to check for both excessive pronation or supination of the feet simultaneously.

Therefore, the sheer sensation on the sole of the foot caused by the user's own weight on the indicator device 26, makes the user aware of the posture of the foot at contact while walking, running, standing or while doing any other activity. This will enable the user to correct the posture of the feet accordingly by rotating the foot in the appropriate direction as shown by the arrows in FIG. 10 through FIG. 13. Whenever these shoe inserts are used, the user is being trained to inculcate the habit of having the correct foot posture.

As a result of this, with the use of these shoe inserts over a period of time, the user would eventually regain or achieve having the correct foot posture. With the problem corrected, the user would no longer need to use these shoe inserts and the problems associated with excessive pronation and supination of the feet will be reduced or removed.

Thus it will be appreciated that these shoe inserts 20, 22, 28 with the step indicating device 26 of this invention provides an efficient and yet economical means by which a person would be able to correct the posture of the feet and thus remove or minimize the problems relating to excessive pronation and supination of the feet.

While the above description contains many specifications, these should not be construed as limitations on the scope of the invention, but rather as an exemplification of one preferred embodiment thereof. Many other variations are possible. For example, the inserts as well as the indicator device can come in different shapes, sizes, materials and colors. The inserts can be coated with a different material. The upper surface of the inserts can be covered with a layer of textile or fabric 30 for additional comfort and aesthetic purposes. The location of the indicator device on the shoe inserts can also vary. The inserts and indicator devices can be made integrally in a single operation or attached together in two or more separate processes. More than one indicator device 26 can be attached to each shoe insert and positioned in different locations on the insert in order to give a specific effect in terms of sensation on the sole of the foot.

The insert and indicator device can be made integrally as part of the actual insole of a footwear. These shoe inserts having the indicator devices can be manufactured for sale as an over-the-counter product or as a custom made-to-measure product to suit specific needs on a case by case basis as recommended by a Podiatrist or Foot Specialist. For a specific requirement, the thickness and stiffness of the shoe inserts, size, shape and location of the indicator device can be varied as needed.

Accordingly, the scope of the invention should be determined not by the embodiments illustrated, but by the appended claims and their legal equivalents.

What is claimed is:

1. An orthotic shoe insert for correcting foot posture, the insert comprising:

An insert having a transverse, cross-sectional U-shaped configuration with a top surface and an opposing bottom surface, the insert having a first thickness under the heel of a user and a second substantially greater thickness along an outer perimeter edge of the insert, the insert made of flexible material;

At least one ball located on the bottom surface at the outer perimeter edge of the insert, the ball made of a solid hard material and having a size greater than the first thickness;

Wherein the ball is an indicator positioned to cause discomfort to the foot of the user when the user's foot does not have correct posture, whereby the user is informed to correct the posture.

2. The insert of claim 1 wherein the insert comprises has an arch support.

3. The insert of claim 1, wherein the insert comprises a ball on a lateral edge and a medial edge of the insert.

4. The insert of claim 1, wherein the insert has a thickness in a heel area that is greater than a thickness of the insert at a mid-foot area.

5. The insert of claim 1, wherein the insert has a thickness in a heel area that gradually thins out towards a toe area of the insert.

\* \* \* \* \*

UNITED STATES PATENT AND TRADEMARK OFFICE
CERTIFICATE OF CORRECTION

PATENT NO.    : 6,732,456 B2
DATED         : June 10, 2004
INVENTOR(S)   : Shakil Hussain It is certified that error appears in the above-identified patent and that said Letters Patent is hereby corrected as shown below:

Column 2,
Line 7, should read -- In accordance with the present invention, an orthotic shoe insert is provided that includes a built-in step indicating device which indicates excessive pronation and supination of the foot. --
Line 10, should read -- In one embodiment, the indicating device is formed of at least one bead on the bottom surface of the insert --.
Line 14, should read -- (a) An orthotic shoe insert that will give an indication to the user the posture or orientation of the foot at ground contact while walking, running, standing or while doing any other activity --.

Column 4,
Line 6, should read -- Where the indicator devices 26 are located near the outer edges of the inserts 20 and 22 as shown in FIGS. 7A and 7B, such shoe inserts are meant for those who suffer from excessive supination or outward roll of the feet --.

Signed and Sealed this

Twenty-seventh Day of July, 2004

JON W. DUDAS
*Acting Director of the United States Patent and Trademark Office*